United States Patent
Vahala et al.

(10) Patent No.: US 11,298,567 B2
(45) Date of Patent: Apr. 12, 2022

(54) TREATMENT PLAN EVALUATION TOOL

(71) Applicant: KONINKLIJKE PHILIPS N.V., Eindhoven (NL)

(72) Inventors: Erkki Tapani Vahala, Hyvinkaa (FI); Lizette Warner, Arlington, TX (US); Kumar Raja Gattamaneni, Bangalore (IN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 623 days.

(21) Appl. No.: 16/096,317

(22) PCT Filed: Apr. 17, 2017

(86) PCT No.: PCT/EP2017/059076
§ 371 (c)(1),
(2) Date: Oct. 25, 2018

(87) PCT Pub. No.: WO2017/186522
PCT Pub. Date: Nov. 2, 2017

(65) Prior Publication Data
US 2019/0126072 A1 May 2, 2019

(30) Foreign Application Priority Data

Apr. 28, 2016 (IN) .............................. 201641014723
Jun. 9, 2016 (EP) ..................................... 16173642

(51) Int. Cl.
*A61N 5/10* (2006.01)
*G01R 33/565* (2006.01)
(Continued)

(52) U.S. Cl.
CPC ......... *A61N 5/1075* (2013.01); *A61N 5/1039* (2013.01); *G01R 33/4812* (2013.01);
(Continued)

(58) Field of Classification Search
None
See application file for complete search history.

(56) References Cited

U.S. PATENT DOCUMENTS 5,036,280 A * 7/1991 Chesavage ............. G01R 33/58
324/308
6,252,401 B1 6/2001 Werthner et al.
(Continued)

OTHER PUBLICATIONS

Barmet et al "Spatiotemporal Magnetic Field Monitoring for MR" Magnetic Resonance in Medicine 60 p. 187-197 (2008).
(Continued)

*Primary Examiner* — Jonathan Cwern
(74) *Attorney, Agent, or Firm* — Sherry Austin

(57) ABSTRACT

It is an object of the invention to improve quality assurance when using MRI images for radiotherapy treatment planning. This object is achieved by a treatment plan evaluation tool A configured for calculating a quality indicator for a radiotherapy treatment plan. The radiotherapy treatment plan originates from a planning image, wherein the planning image is an MRI image acquired under a presence of a main magnetic field having a magnetic field inhomogeneity. The treatment plan evaluation tool is further configured to receive information about the magnetic field inhomogeneity and the treatment plan evaluation tool is further configured to calculate the quality indicator based on the information about the magnetic field homogeneity.

20 Claims, 3 Drawing Sheets

(51) Int. Cl.
*G01R 33/58* (2006.01)
*G01R 33/48* (2006.01)

(52) U.S. Cl.
CPC ....... *G01R 33/56563* (2013.01); *G01R 33/58* (2013.01); *A61N 2005/1074* (2013.01); *G01R 33/56536* (2013.01)

(56) References Cited

U.S. PATENT DOCUMENTS

| | | |
|---|---|---|
| 8,050,477 B2 | 11/2011 | Spies |
| 8,131,047 B2 | 3/2012 | Li |
| 8,582,845 B2 | 11/2013 | Ootsuka |
| 8,725,232 B2 | 5/2014 | Vahala |
| 9,662,512 B2 | 5/2017 | Vahala |
| 2002/0057086 A1 | 5/2002 | Mueller et al. |
| 2003/0178996 A1* | 9/2003 | Schreck ........... G01R 33/56563 324/307 |
| 2007/0018645 A1 | 1/2007 | Wang et al. |
| 2013/0235969 A1 | 9/2013 | Winter et al. |
| 2013/0315463 A1 | 11/2013 | Vilsmeier et al. |
| 2014/0266198 A1 | 9/2014 | Tadic et al. |
| 2014/0327440 A1* | 11/2014 | Nakanishi ............. A61B 5/055 324/309 |
| 2015/0088449 A1 | 3/2015 | Foxall et al. |
| 2016/0310761 A1* | 10/2016 | Li ........................... G06K 9/52 |

OTHER PUBLICATIONS

Baldwin et al "Characterization Prediction and Correction of Geometric Distortion in 3T MR Images" Med. Phys. 34 (2) Feb. 2007 p. 388-399.

Sandgren "Development of a Quality Assurance Strategy for Magnetic Resonance Imaging in Radiotherapy" Masters Thesis, Jul. 2, 2015.

Chen et al "Investigation of MR Image Distortion for Radiotherapy Treatment Planning of Prostate Cancer" Phys. Med. Biol. 51 (2006) p. 1393-1403.

Walker et al "MRI Distortion Considerations for MRI Based Radiotherapy Treatment Planning" Australasian Physical & Engineering Sciences in Medicine, Mar. 2014, vol. 37, Issue 1. pp. 103-113.

Crijns et al "Real-Time Correction of Magnetic Field Inhomogeneity-Induced Image Distortions for MRI—Guided Conventional and Proton Radiotherapy" Phys. Med. Biol.. 56 (2011) p. 289-297.

* cited by examiner

TREATMENT PLAN EVALUATION TOOL

CROSS REFERENCE TO RELATED APPLICATIONS

This application is a U.S. national phase application of International Application No. PCT/EP2017/059076, filed on Apr. 17, 2017, which claims the benefit of EP Application Serial No. 16173642.6 filed on Jun. 9, 2016 and IN Application Serial No. 201641014723 filed April 28, 2016 and is incorporated herein by reference.

FIELD OF THE INVENTION

The invention relates to the field of Magnetic Resonance Imaging (MRI) and more specifically to the use of MRI for therapy planning, especially radiotherapy planning.

BACKGROUND OF THE INVENTION

Magnetic resonance imaging (MRI) is becoming of increased importance in the field of therapy, especially in the field of radiotherapy. MRI may help to better distinguish tumor tissue from healthy tissue. In addition it may help in improving delineations of organs at risk (OAR). This makes it interesting to use MRI for treatment planning. To facilitate MRI based radiotherapy planning, MRI images may be used to generate pseudo computed tomography (CT) images or attenuation maps. In the context of this document MRI images that contribute to a generation of a radiotherapy plan are defined as MRI planning image. The planning MRI image could for example be a pseudo CT image or attenuation map, the planning MRI image could also be an MRI image used to generate a pseudo CT or attenuation map, also the planning image could be one or more MRI images that are configured to be used for delineation of structures of interest.

One drawback of using MRI in a therapy setting is that MRI may suffer from reduced geometric accuracy compared to for example CT. This may affect the quality of MRI based treatment.

US2014/0266198A1 describes methods to determine the geometric accuracy in a region of interest (ROI). The method comprises deriving a set of 3D vectors describing the distortion within an ROI covered by a phantom. The characterized image distortions may be used for shimming or image correction. The image correction method can be integrated in a treatment planning system (TPS).

SUMMARY OF THE INVENTION

It is an object of the invention to improve quality assurance when using MRI images for treatment planning. This object is achieved by a treatment plan evaluation tool according to claim 1. This object is also achieved by a method according to claim 8.

Commonly, a radiotherapy treatment plan is generated by setting goals to be achieved. An example of such a goal is a minimum or maximum dose that may be given to a-a selected structure. Such structure could for example be an organ at risk or planned target volume (PTV), which is tumor seen on the image plus some margins). Depending on several factors like e.g. on a radiosensitivity of the structure and its location a certain treatment goal for the structure will be set. However, due to geometric inaccuracies caused by a main magnetic field, which was used to generate a planning MRI image, the exact location and / or volume of the structure may be different than it was assumed to be. When evaluating if a treatment goal has been met by the treatment planning system, the geometric accuracy of the MRI planning image should be considered. Without direct knowledge of the volume where distortion stays within acceptable levels, the user is forced to measure distance from the MR isocenter or rely on visual inspection if he or she suspects that important tissue volumes remain outside the homogeneous volume. This is inefficient and it is likely not very accurate. The invention addresses these issues by calculating a quality indicator for the treatment plan based on the information about the magnetic field homogeneity. In this way the effect of the geometric inaccuracy on the quality of the treatment plan can be easily determined. In this way quality assurance may be improved According to embodiments of the invention, the treatment plan evaluation tool is configured to calculate the quality indicator for the treatment plan using one or more of the following inputs: amount of distortion, prescribed dose, planned dose (which preferably meets the clinical goals and is preferably close to the prescribed dose), tissue sensitivity, radiation beam orientation, distance between organ at risk and tumor, type of organ at risk or tissue represented in the planning image. The terms radiotherapy treatment plan and treatment plan are considered to be equivalent herein. These parameters affect treatment outcome either in terms of toxicity or tumor control. One could be more cautious when a certain structure, especially an OAR has a high tissue or radiation sensitivity. Also, one could be more cautious with so-called serial OARs compared to so-called parallel OARs. Therefore, it is advantageous if geometric inaccuracies have a larger effect on the quality indicator for serial structures and / or structures with a higher radiation sensitivity. It is also advantageous to take beam orientation into account when calculating the quality indicator. Geometric inaccuracies are mainly relevant if they are located in a beam path, especially when they are located parallel to the treatment beam. Therefore, it is advantageous to give geometric inaccuracies a higher weight when they are located at these positions. In addition a warning may be displayed to a user of the system, that geometric accuracies occur within the radiation beam path. This may be a reason for the user to adjust a beam orientation. It is also advantageous to take a distance between an OAR and the tumor into account when calculating the quality indicator. The closer the OAR is to the tumor, the larger an effect of geometric inaccuracy will be. Therefore, it is also advantageous to take this into account when calculating the quality indicator, e.g. by weighing the geometric inaccuracy by the distance between the tumor and the specific OAR. One could calculate the quality indicator per structure. This is insightful, because in this way it can be easily assessed at what locations problems occur. Alternatively or additionally, one could calculate one quality indicators for the overall treatment plan. This could for example be achieved by combining quality indicators for different structures by means of weighted contribution.

According to further embodiments of the invention the treatment plan evaluation tool is configured to compare a geometric distortion caused by the magnetic field inhomogeneity at a location of an organ with a preset limit for this geometric distortion. The outcome of this comparison could be the quality indicator. The treatment plan evaluation tool could be further configured to provide a warning to a user if the geometric distortion exceeds the preset limit. This embodiment is advantageous, because it may help in preventing that less optimal treatments will be delivered to patients.

According to further embodiments, the treatment plan evaluation tool is configured to use the information about the magnetic field homogeneity to geometrically correct the MRI planning image. This embodiment is advantageous, because it may result in better treatment plans.

According to further embodiments of the invention the treatment plan evaluation tool comprises a treatment planning unit, configured to generate a treatment plan based on the planning image. This embodiment is advantageous, because in this way, insights obtained by assessing the quality indicator can be easily used to improve the treatment plan.

According to another aspect the invention is a method for quality assurance, wherein the method comprises the following steps:

determining a magnetic field inhomogeneity of a magnetic resonance imaging system and;
   acquiring one or more magnetic resonance images with the magnetic resonance imaging system, wherein one or more of the one or more magnetic resonance images result in a planning image and;
   using the planning image to generate a treatment plan and;
   using information about the magnetic field inhomogeneity to calculate a quality indicator for the treatment plan.

According to embodiments of the invention the method for quality assurance as a determination of the magnetic field inhomogeneity is used as an input for the calculation of a quality indicator for multiple patients. This embodiment is advantageous, because it may allow a faster quality assurance procedure.

According to embodiments of the invention for each patient the magnetic field inhomogeneity is determined and used as an input for the calculation of the quality indicator. This embodiment is advantageous, because it may improve the accuracy of the quality assurance procedure.

The term "quality factor" as used herein may be considered to be a numerical score or value which is assigned to a radiotherapy treatment plan. The quality factor may be used in a number of different ways. It may be displayed to human operator so that the human operator can easily interpret how well the radiotherapy treatment plan protects healthy tissue of a subject. The quality factor may also be interpreted as a quantitative measure of how well the radiotherapy treatment plans protects healthy tissue of the subject during a radiotherapy treatment.

As the quality factor is a quantitative measure it may be used by an optimization algorithm to optimize the radiotherapy treatment plan to modify the radiotherapy treatment plan and improve the radiotherapy treatment plan. For example alternate beam paths for candidate radio therapy treatment plans can evaluated using the radiotherapy treatment plan and the beam paths which result in the best quality factor can be used to select which candidate radiotherapy treatment plan is selected to be the radiotherapy treatment plan.

A treatment plan evaluation tool as used herein encompasses a processor and or controller configured for calculating a quality indicator for a treatment plan. The treatment plan evaluation tool may be for example incorporated into a magnetic resonance imaging system and/or a radiotherapy treatment system.

It is understood herein that references to the magnetic field homogeneity and the magnetic field inhomogeneity are equivalent. Both are a measure or description of how the magnetic field varies spatially.

These and other aspects of the invention will be apparent from and elucidated with reference to the embodiments described hereinafter.

DETAILED DESCRIPTION OF THE INVENTION

Figure 1:
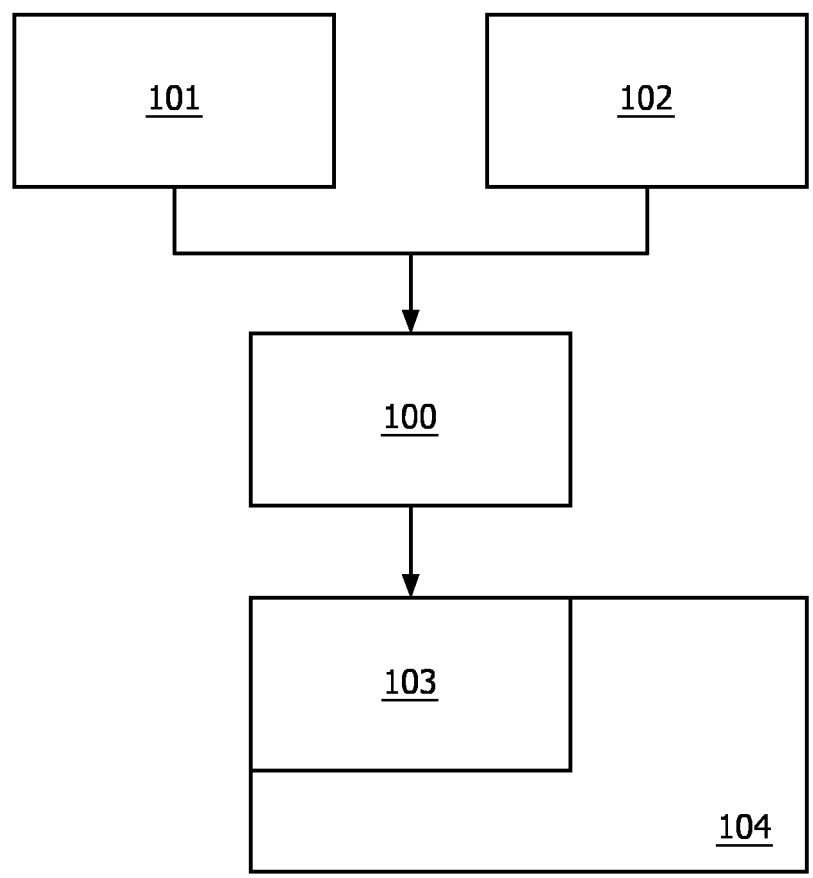
FIG. 1 diagrammatically shows a treatment plan evaluation tool.

FIG. 1 diagrammatically shows a treatment plan evaluation tool 100. The treatment plan evaluation tool 100 receives information about the magnetic field homogeneity 101. This information could for example be a three-dimensional distortion map from an MRI imaging volume. The distortion map can be generated (FIG. 3, 301) during a quality assurance check, one can use for example a planar 2D phantom as it traverses through the imaging volume. Known locations of small marker spheres on the phantom and the tabletop can be used together with acquired MRI images to deduce distortions. This generates a 3D distortion map over a specific field of view that can then be used to spatially isolated magnetic and gradient distortions based on location alone. Additionally one can acquire patient specific distortions to generate a patient customized distortion correction map. In addition to or alternatively to the 2D phantom, one can also use large 3D phantoms already known in the art to forego tabletop movement. In order to generate a distortion map information with the patient-induced distortions in place, one of the possible implementations is: the system can use micro-coils or similar small probes on known locations around the patient and fit the spherical harmonics to measurement points to estimate the distortions due to susceptibility artifacts stemming from the patient, similarly to MR scanner shimming procedures already known in the art [Magnetic Resonance in Medicine 60:187-197 (2008). Spatiotemporal Magnetic Field Monitoring for MRChristoph Barmet, Nicola De Zanche, and Klaas P. Pruessmann].

The distortion map can be transmitted either as DICOM overlays, masking 3D DICOM image series, DICOM mesh of distortion isocontours (e.g., 1 mm distortion isocontour, 3 mm isocontour, . . . ), named DICOM RT Struct 2D contours, or in proprietary mesh format with meta-data to help in automating the subsequent display operations.

Figure 3:
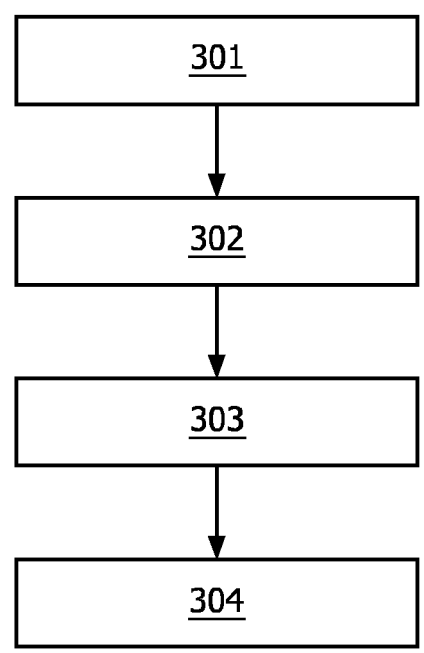

Based on the information about the magnetic field homogeneity 101 the treatment plan evaluation tool 100 calculates a quality indicator 103 (step 304, FIG. 3). This quality factor can displayed to a user by means of a display 104. Also the distortion map itself can be visualized and displayed to the user, for example by means of a checkerboard overlay or alpha blend on top of the planning image. In a simple embodiment the quality indicator 103 is the result of a comparison between the geometric inaccuracies with a preset limit for these geometric inaccuracies. In more advanced embodiments other factors 102 are also taken into account when calculating the quality indicator. These factors could for example be prescribed dose, planned dose, tissue sensitivity, radiation beam orientation, distance between organ at risk and tumor, type of organ at risk or tissue represented in the planning image. One way of doing this is by weighing the geometric inaccuracies by one or more of the above mentioned factors. Preferably this is done for both the tumors and each of the relevant OARs.

Figure 2:
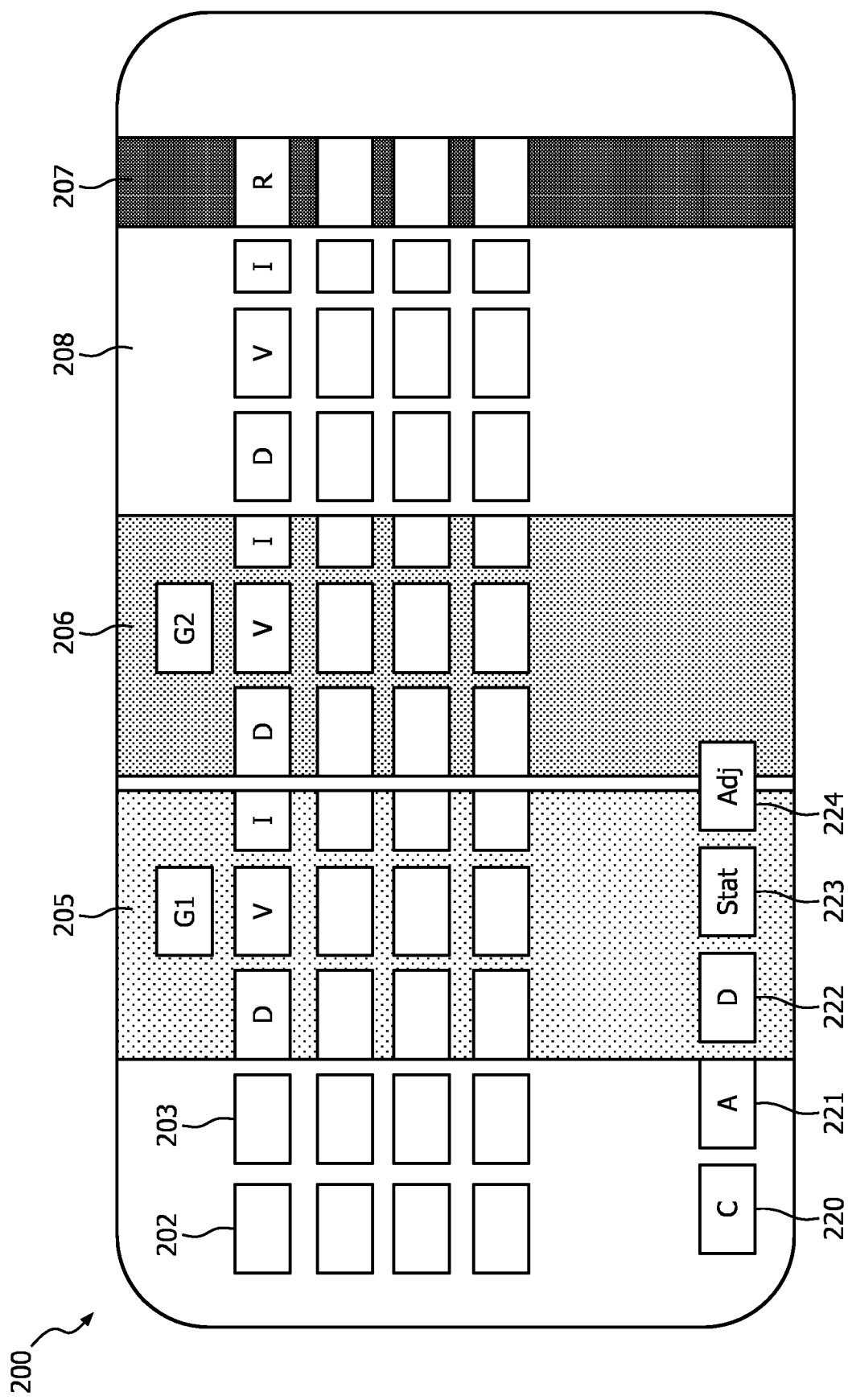
FIG. 2 diagrammatically shows an example of how the quality indicator could be integrated in a so-called scorecard and FIG. 3 diagrammatically shows a method according to the invention.

FIG. 2 shows an example of how the quality indicator could be integrated in a so-called scorecard 200. Treatment goals G1 205, G2 206 can be set in the scorecard 200 for different regions of interest/structures 202. G1 relates to a primary treatment goal and G2 relates to a secondary treatment goal, which is less stringent than the primary treatment goal G1. The treatment goals relate to what volume percentage (column V) of the structure 202 should receive what dose (column D, e.g. minimal, maximum, mean dose). In addition, in the scorecard according to FIG. 2 one or more inputs can be given for the geometric accuracy (column I). These inputs can be related to prescribed dose, planned dose, tissue sensitivity, radiation beam orientation, distance between organ at risk and tumor, type of organ at risk or tissue represented in the planning image 102. The inputs could for example be weighing factors. However, they could also be pre-set limits for the geometric inaccuracy. For quality indicators, different organs can have preset values that specify how much of the dose volume is allowed to lie outside the (1 mm/3 mm) homogeneous volume before triggering a warning cue or a downright error condition. The volume can be approximately distortion-corrected based on the distortion map. It is also possible to calculate a more abstract quality indicator, such as a dose volume where the volume value is weighted by a factor that is dependent of the interpolated distortion at each voxel location. These indicators can be displayed, for example, on the plan review scorecard with color coding (green, yellow, red) or with a pass/fail criteria (e.g. in column R, 207 see below). A warning can be provided if the quality indicator falls outside the scope of a preset limit. The warning/error can also acts as a short-cut link to view a slice that contains largest volume outside the homogeneous volume to facilitate reviewing.

After a treatment plan has been calculated in column 208 for each structure 202 will be displayed what the planned dose (column D) is for what volume percentage (column V) of the structure. In addition the (weighted) geometric accuracy or quality indicator for the structure will be displayed (column I). This could for example be a mean or maximum distortion for the structure. In the last column R 207 it will be displayed whether the primary goal, the secondary goal or none of the goals has been achieved. The lower buttons 220-225 can be used to initiate a computation of a treatment plan based on the goals set C 220, to add a treatment goal A 221, to delete a treatment goal D 222 or to view statistics for a specific structure stats 223, e.g. by means of displaying a dose volume histogram. Button Adj 224 can be used in addition or alternatively to providing inputs for the geometric accuracies in columns I. This button can be used to adjust the treatment goals G1, G2 in order to take the geometric inaccuracy into account. For example based on the distortion map one or more of the treatment goals can be adjusted automatically, e.g. the delineated volume could be automatically changed, or the volume goal could be updated FIG. 3 diagrammatically shows a method according to the invention. The method comprises the following steps:

Step 301: determining a magnetic field inhomogeneity of a magnetic resonance imaging system. In one embodiment of the invention, the distortion map is generated during the daily quality assurance-check and re-used with each patient. In another embodiment of the invention, the distortion map is generated or augmented with measurements from the patient already under MR examination. In another embodiment of the invention, the distortion map of any of the embodiments above is used to rectify the images acquired from the patients by deforming the voxels according to the distortion vector fields of distortion map.

Step 302: acquiring one or more magnetic resonance images with the magnetic resonance imaging system, wherein one or more of the one or more magnetic resonance images result in a planning image and;

Step 303: using the planning image to generate a treatment plan and;

Step 304: using information about the magnetic field inhomogeneity to calculate a quality indicator for the treatment plan. The quality factor can be a measure of the goodness of the image accuracy, so the inputs would be the distortions, dose planned to be delivered and weighting by organ type. Some organs are more critical than others so if there are distortions in the vicinity of critical structures, those organs or locations need to be weighted higher—if there are distortions on those locations, the physician can be informed by means of a score card or visually on the image, for example.

It should be noted that in some cases the quality indicator can be calculated before the treatment plan is calculated, e.g. in cases where the quality indicator is based only on the amount of geometric distortion.

Whilst the invention has been illustrated and described in detail in the drawings and foregoing description, such illustrations and description are to be considered illustrative or exemplary and not restrictive; the invention is not limited to the disclosed embodiments.

The invention claimed is:

1. A treatment plan evaluation tool comprising a processor and/or controller configured for calculating a quality indicator for a radiotherapy treatment plan,
wherein the radiotherapy treatment plan originates from a planning image, wherein the planning image is a magnetic resonance imaging (MRI) image acquired under a presence of a main magnetic field having a magnetic field inhomogeneity;
wherein the treatment plan evaluation tool is further configured to receive information about the magnetic field inhomogeneity and wherein the treatment plan evaluation tool is further configured to calculate the quality indicator for the radiotherapy treatment plan by comparing the magnetic field inhomogeneity within an organ with a preset limit for the magnetic field inhomogeneity;
wherein the treatment plan evaluation tool is configured to weight the quality indicator for the radiotherapy treatment plan by organ type, wherein distortions in the planning image caused by the inhomogeneity in the magnetic field get a higher weight when they are at or near a sensitive or critical structure or organ; and
wherein the treatment plan evaluation tool is further configured to weight the quality indicator for the radiotherapy treatment plan by radiation beam orientation.

2. The treatment plan evaluation tool of claim 1, configured to calculate the quality indicator for the radiotherapy treatment plan using one or more of the following inputs: amount of distortion, prescribed dose, planned dose, tissue sensitivity, distance between organ at risk and tumor, type of organ at risk or tissue represented in the planning image.

3. The treatment plan evaluation tool of claim 1, configured to compare a geometric distortion caused by the magnetic field inhomogeneity at a location of an organ with a preset limit for the geometric distortion, wherein the treatment plan evaluation tool is configured to provide a warning to a user if the geometric distortion exceeds the preset limit.

4. The treatment plan evaluation tool of claim 1, configured to display the quality indicator to a user.

5. The treatment plan evaluation tool of claim 1, configured to use the information about the magnetic field inhomogeneity to geometrically correct the planning image.

6. The treatment plan evaluation tool of claim 1, comprising a treatment planning unit, configured to generate a radiotherapy treatment plan based on the planning image.

7. The treatment plan evaluation tool of claim 6, wherein the treatment planning unit is further configured to generate the radiotherapy treatment plan by optimizing the quality indicator.

8. The treatment plan evaluation tool of claim 1, wherein the treatment plan evaluation tool is further configured to receive the information about the magnetic field homogeneity inhomogeneity from a three dimensional distortion map of at least a portion of an MRI imaging volume from which the planning image is obtained.

9. The treatment plan evaluation tool of claim 8, wherein the three dimensional distortion map of the MRI imaging volume from which the planning image is obtained is generated from a planar two-dimensional phantom as it passes through the MRI imaging volume.

10. The treatment plan evaluation tool of claim 8, wherein the three dimensional distortion map of the MRI imaging volume from which the planning image is obtained is a patient-customized map which reflects patient-specific distortions.

11. A method, comprising:
determining a magnetic field inhomogeneity of a magnetic resonance imaging system;
acquiring one or more magnetic resonance images with the magnetic resonance imaging system, wherein one or more of the one or more magnetic resonance images result in a planning image;
using the planning image to generate a radiotherapy treatment plan; and
a treatment plan evaluation tool comprising a processor and/or controller using information about the magnetic field inhomogeneity to calculate a quality indicator for the radiotherapy treatment plan by comparing the magnetic field inhomogeneity within an organ with a preset limit, wherein the quality indicator for the radiotherapy treatment plan is weighted by organ type and wherein distortions in the planning image caused by the inhomogeneity in the magnetic field get a higher weight when they are at or near a sensitive or critical structure or organ, wherein the treatment plan evaluation tool is further configured to weight the quality indicator for the radiotherapy treatment plan by radiation beam orientation.

12. The method of claim 11, wherein a determination of the magnetic field inhomogeneity is used as an input for the calculation of a quality indicator for multiple patients.

13. The method of claim 12, wherein for each patient the magnetic field inhomogeneity is determined and used as an input for the calculation of the quality indicator.

14. The method of claim 11, wherein the information about the magnetic field inhomogeneity is used to geometrically correct the one or more magnetic resonance images.

15. The method of claim 11, wherein the quality indicator is calculated using one or more of the following inputs: amount of distortion, prescribed dose, planned dose, tissue sensitivity of tissue represented in the planning image.

16. The method of claim 11, wherein the quality indicator is weighted by organ type and wherein distortions in the planning image caused by inhomogeneities in the magnetic field get a higher weight when they are at or near a sensitive or critical structure or organ.

17. The method of claim 11, wherein the planning image is generated at least partially by optimizing the quality indicator.

18. The method of claim 11, comprising a step of displaying the quality indicator to a user.

19. The method of claim 11, wherein determining the magnetic field inhomogeneity of the magnetic resonance imaging system comprises obtaining a three dimensional distortion map of at least a portion of an MRI imaging volume from which the planning image is obtained.

20. The method of claim 19, wherein obtaining the three dimensional distortion map of at least the portion of the MRI imaging volume from which the planning image is obtained comprises generating the three dimensional distortion map from a planar two-dimensional phantom as it passes through the MRI imaging volume.

* * * * *